United States Patent

Inouye

Patent Number: 5,289,930
Date of Patent: Mar. 1, 1994

[54] EVAPORATION CLOSURE
[75] Inventor: Kenneth K. Inouye, Palo Alto, Calif.
[73] Assignee: Syntex (U.S.A.) Inc., Palo Alto, Calif.
[21] Appl. No.: 794,751
[22] Filed: Nov. 19, 1991
[51] Int. Cl.[5] .................. B65D 51/04; B65D 71/00
[52] U.S. Cl. ................... 215/235; 215/237; 220/254; 220/337; 206/223; 222/556; 222/562; 222/517
[58] Field of Search ............... 215/235, 236, 237, 238, 215/239, 240, 242; 220/263, 264, 335, 337, 338, 341, 254; 206/223; 222/545, 556, 562, 563, 517

[56] References Cited

U.S. PATENT DOCUMENTS

| | | | |
|---|---|---|---|
| 1,472,398 | 10/1923 | Longman | 215/352 X |
| 1,588,652 | 6/1926 | Brown | 215/352 X |
| 1,687,689 | 10/1928 | Petry | 215/352 X |
| 1,794,987 | 3/1931 | Sebolt | 220/335 X |
| 2,111,186 | 3/1938 | Jenks | 215/235 X |
| 2,126,087 | 8/1938 | Berry et al. | 215/237 |
| 2,136,123 | 11/1938 | Baron | 215/235 X |
| 2,196,530 | 4/1940 | Johnson et al. | 220/335 X |
| 3,022,925 | 2/1962 | Daniell | 222/517 |
| 3,052,386 | 9/1962 | Martorelli | 222/517 |
| 3,098,721 | 7/1963 | Jewell et al. | 23/259 |
| 4,305,515 | 12/1981 | Tontarelli | 215/244 |
| 4,455,280 | 6/1984 | Shinohara et al. | 422/63 |
| 4,805,790 | 2/1989 | Leonetti et al. | 215/235 |
| 5,029,701 | 7/1991 | Roth et al. | 206/223 X |
| 5,065,877 | 11/1991 | Karppinen et al. | 215/239 |
| 5,150,802 | 9/1992 | Jeffers | 215/235 |

FOREIGN PATENT DOCUMENTS 3346517 8/1984 Fed. Rep. of Germany .
820708 11/1937 France .

Primary Examiner—Allan N. Shoap
Assistant Examiner—Vanessa Caretto
Attorney, Agent, or Firm—Mark L. Bosse; Theodore J. Leitereg

[57] ABSTRACT

An evaporation closure is disclosed. One embodiment of the closure includes a cap, made of pliable material, which in turn includes a top wall having an opening, a skirt downwardly depending from the top wall and having a threadless internal wall adapted to slip on and sealingly engage a container, and biasing means integral with the skirt; and an elongated arm, which in turn includes a means for sealing the opening, pivotally attached to the cap for movement between a first position wherein the sealing means seals the opening and a second position wherein the sealing means does not seal the opening, the arm being biased toward the first position by the biasing means. Such a closure is useful for minimizing evaporation from containers, particularly automated clinical analyzer reagent bottles.

A kit including in packaged combination component parts of the evaporation closure is also disclosed. Such a kit is useful for conveniently assembling the evaporation closures of the present invention.

12 Claims, 5 Drawing Sheets

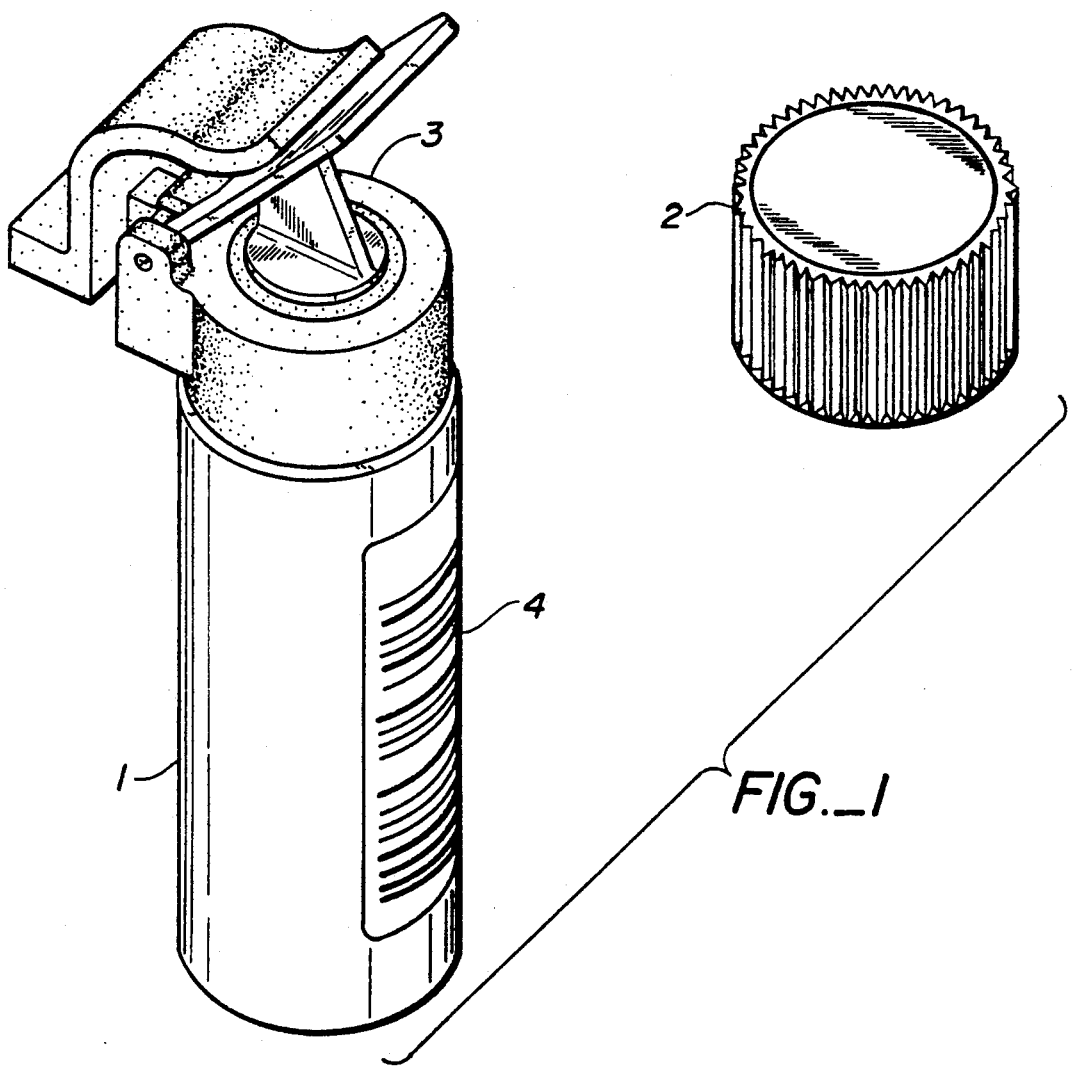
FIG._1

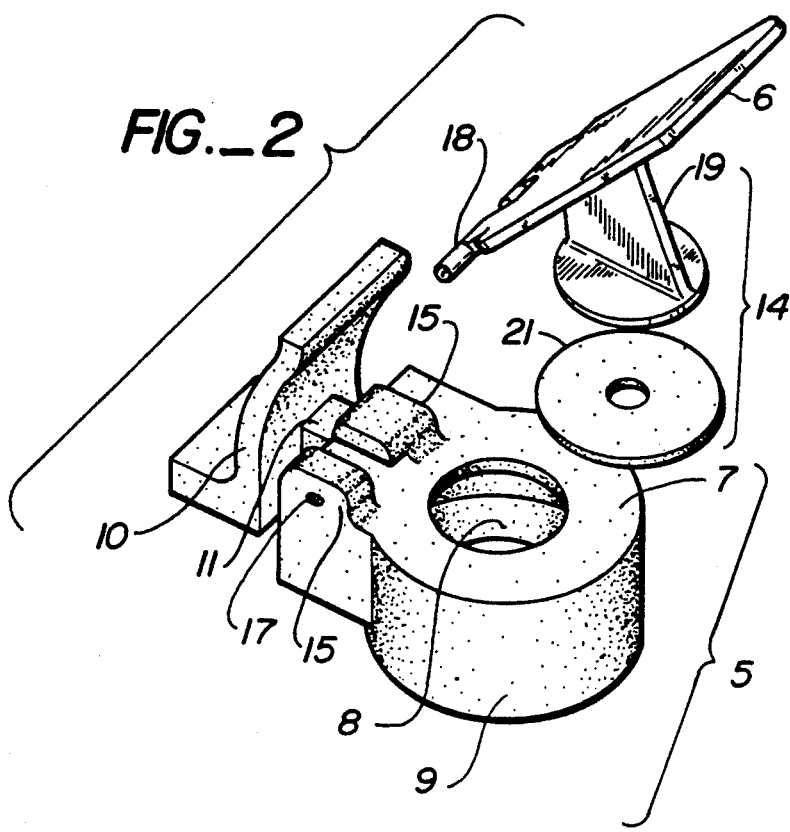
FIG._2
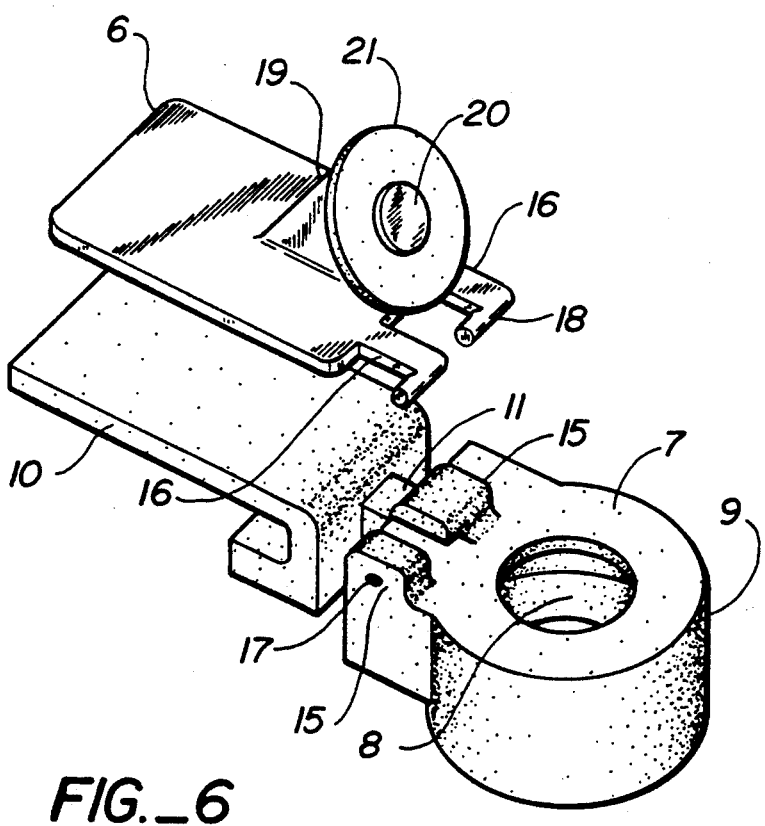
FIG._6

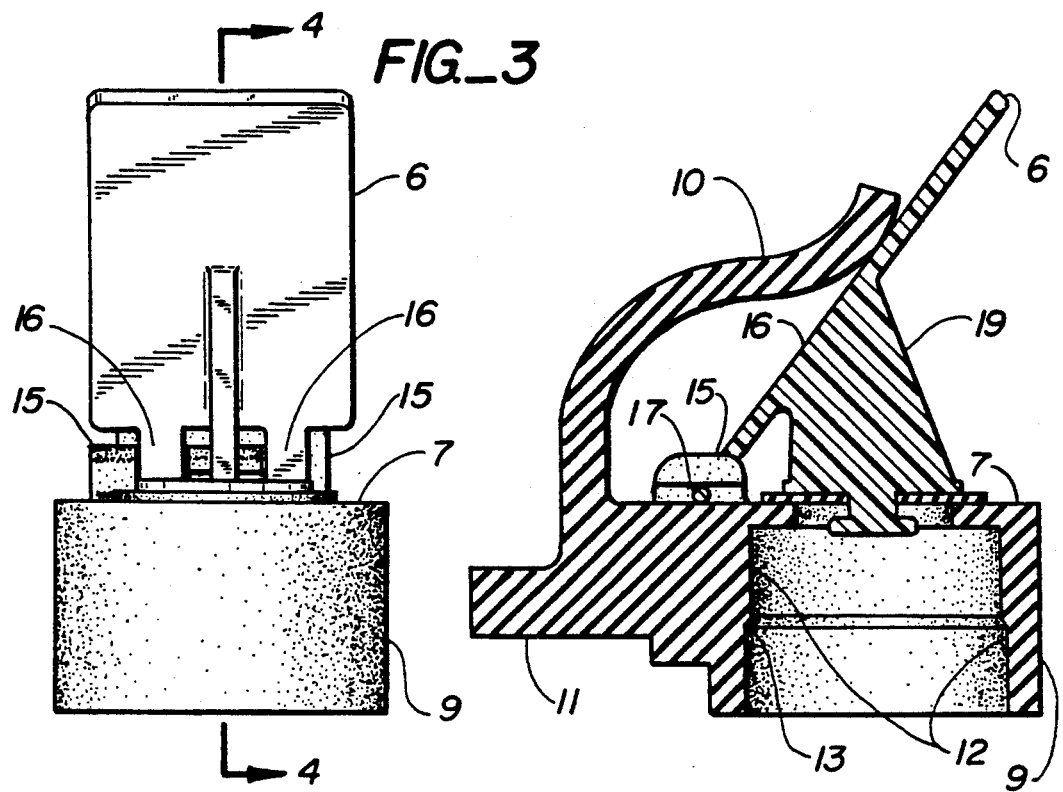
FIG._3
FIG._4
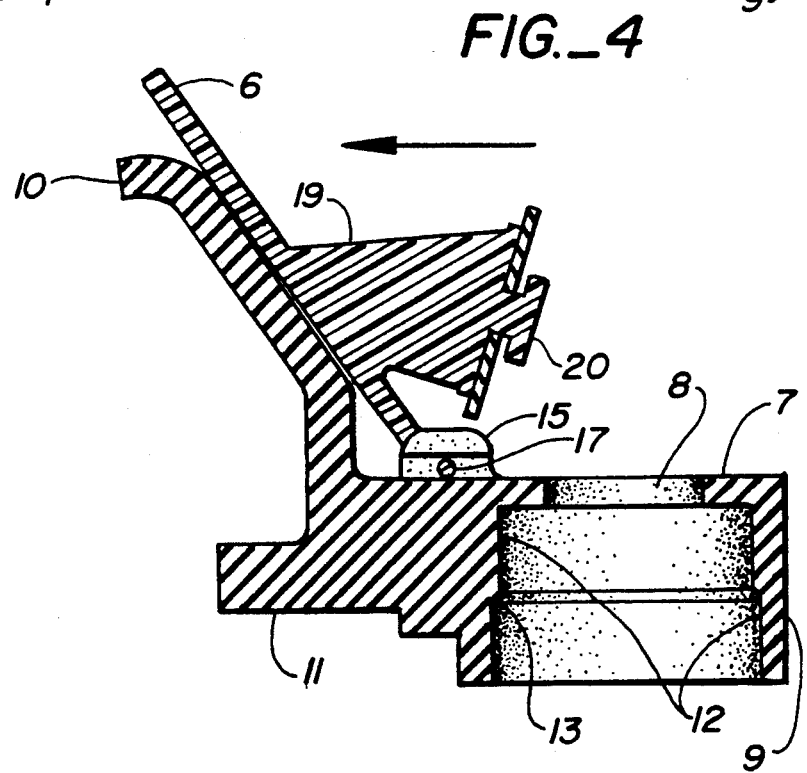
FIG._5

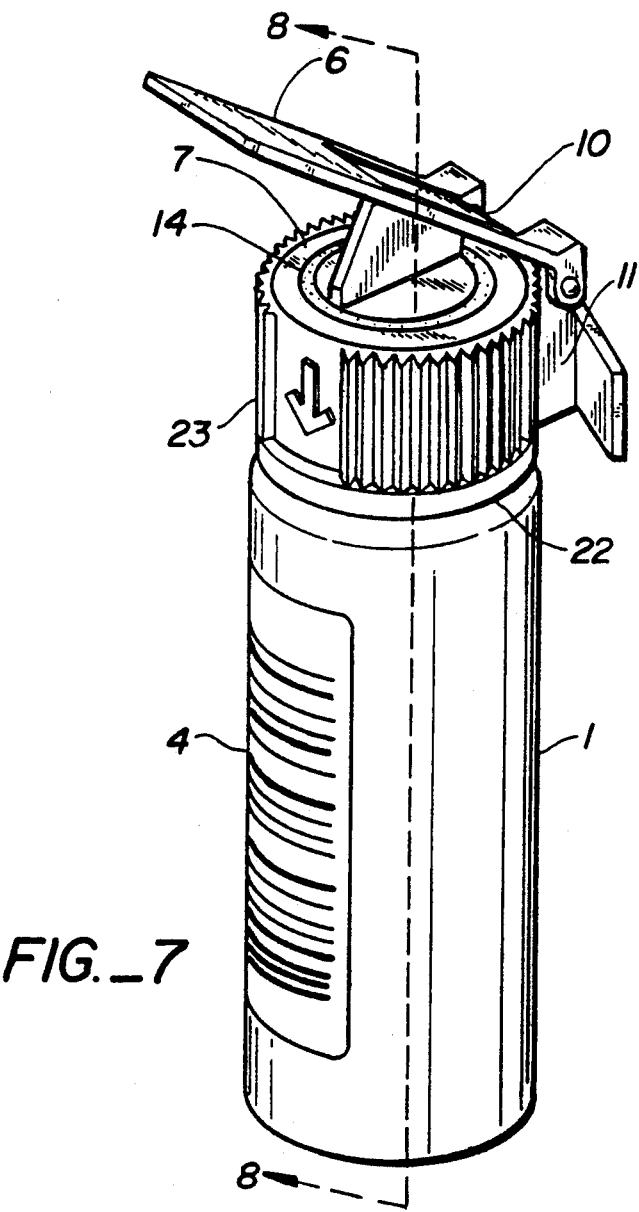
FIG._7

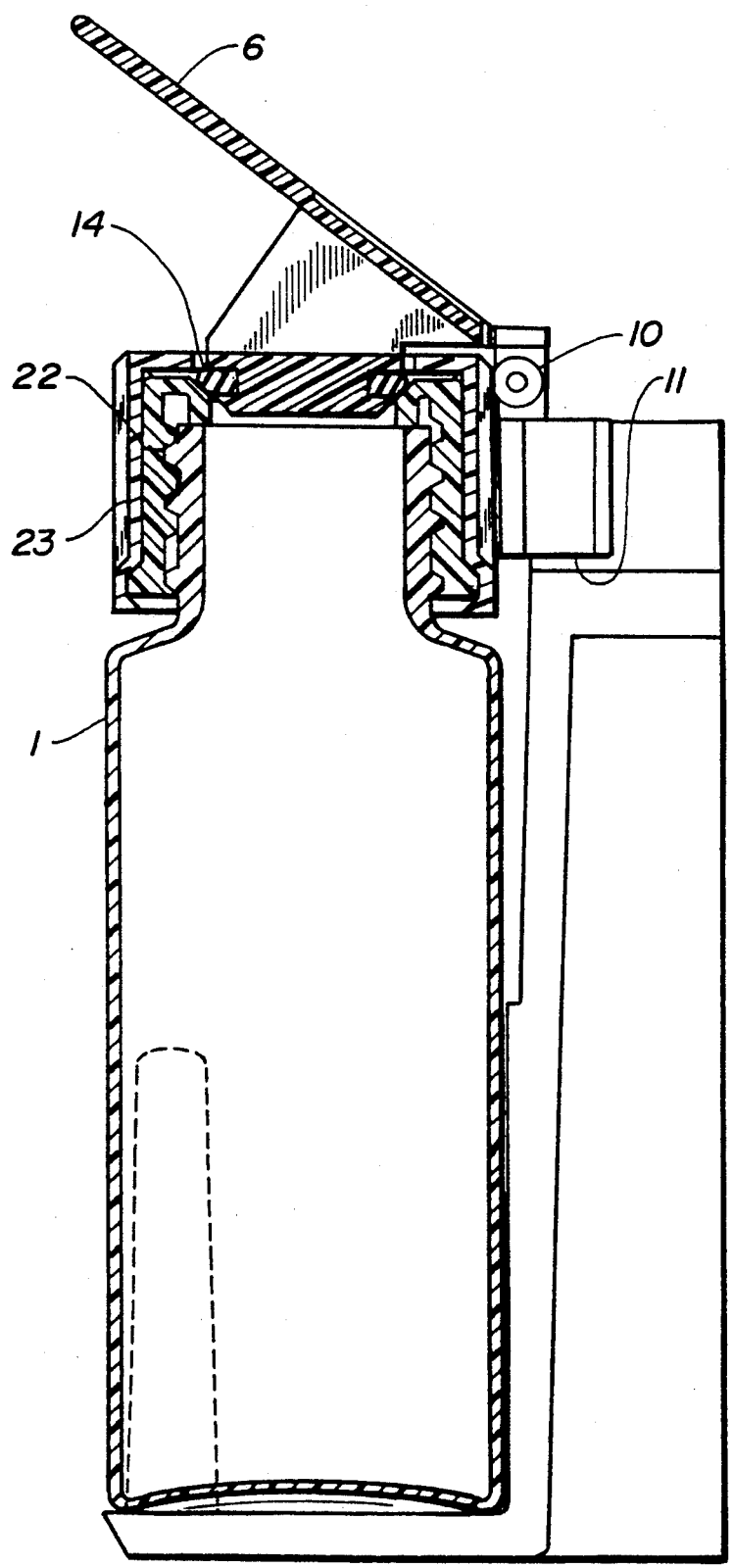

EVAPORATION CLOSURE

BACKGROUND OF THE INVENTION

Field of the Invention

The present invention relates to evaporation closures, particularly to evaporation closures for clinical analyzer reagent bottles.

Clinical analyzers are widely used for the analysis of chemical and biological samples. Operational simplicity and cost effectiveness are important aspects of clinical analyzer utility. Improvements in either the ease of use or cost per test for a clinical analyzer can significantly impact its value in the market place.

Chemical and biological reagents are commonly employed together with clinical analyzers. Such reagents are used to perform chemical and biological reactions necessary for the successful analysis of a sample. Frequently, a significant portion of the cost and operator time required to perform a given analysis can be related to the selection, manipulation and losses of such reagents.

Typically, reagent containers for clinical analyzers are either un-capped during use or are covered by puncturable sealing means such as elastomeric septa supported by metallic or plastic caps. Reagents in un-capped containers or in containers capped by punctured closures are exposed to the environment of the analyzer. Such exposure can lead to contamination of the analyzer, which in turn can cause damage or impaired functioning or can contaminate the analyzer in such a way as to lead to inaccurate results on future assays. More importantly, such exposure can effect the reagents themselves. If a component of the reagent is sensitive to air or moisture, for example, then it can be destroyed or its functioning can be impaired. If one component is more volatile than another, then its concentration relative to less volatile components can be altered in such a way as to adversely impact the assay to be performed. Generally, exposure of assay reagents can significantly impact the cost and reliability of a given assay.

Methods to reduce such adverse impacts have previously required complex and/or costly sealing means such as stoppers or pipettes used as stoppers or complex, device specific reagent containers. Some of these techniques require that the operator spend time manipulating the container system and others require that the reagent bottle be used with the specific instrument for which it was designed.

Another practical disadvantage of some closure systems is that they require careful positioning of a bar code or other label on the reagent container after the closure has been affixed. This is inconvenient because it requires an operator to inspect a container-closure combination and individually affix the label. Typically, this problem has required the use of device specific reagent bottles wherein the shape of the bottle allowed it to connect to the closure in only one way, thereby increasing cost and complexity.

The present invention provides a solution to these and other problems by providing cost effective, simple, machine operable closures that allow cap position independent label positioning. The closures of the present invention improve the ease of handling and life expectancy of chemical and biological reagents and, therefore, are useful in any application involving such reagents.

Brief Description of Related Art

Baisch, M.; Rüsbüldt, H.; U.S. Pat. No. 4,751,186 (Jun. 14, 1988; filed Feb. 15, 1985) discloses a reagent container rack for use in a chemical analysis system (see Figure). The sealing means disclosed is perforated prior to use and once perforated does not provide an evaporation seal. Placement of bar code labels on the rack depends on the unique shape of the entire container assembly.

Kelln, N.G.; Tiffany, T.O.; U.S. Pat. No. 4,764,342 (Aug. 16, 1988; filed Feb. 27, 1985) discloses a reagent handling system for use in analysis systems. The system relies on a reagent container having a probe puncturable membrane (see FIGS. 1-8). Once punctured, the membrane is no longer a sealing means and is said to be supplemented with a second probe puncturable web contained in a cap. Placement of bar code labels on the container depends on the unique shape of the entire container assembly.

Harris, A.M.; U.S. Pat. No. 4,738,826 (Apr. 19, 1988; filed Jan. 29, 1986) discloses a reagent container for use in a reagent metering and delivery device. The sealing means is a movable plunger or piston that moves to reduce the volume of the container and thereby dispense the reagent. The container provides no means for conveniently locating a bar code label.

Saxon, R.L.; Zeger, L.; Horbatt, K.; U.S. Pat. No. 4,927,765 (May 22, 1990; filed Feb. 29, 1988) discloses an automatic reagent dispenser. The system includes a reagent bottle cap (see FIGS. 4-6). The cap lacks an evaporation closure or sealing means. The system relies on a pipette tip associated with each reagent bottle. The individual bottles are stoppered by the dedicated pipette tip while in the instrument for short times. However, an auxiliary stopper (not disclosed) is said to be provided to seal the cap when the bottle is stored or when the pipette life is exhausted.

Andersen, M.R.; Tiffany, T.O.; Gangitano, M.J.; U.S. Pat. No. 4,961,906 (Oct. 9, 1990; filed Jun. 27, 1988) discloses a liquid handling system for automated chemical analysis systems. The system includes a reagent container having a cover with ports (see FIGS. 6-8). The ports lack an evaporation closure or sealing means. The container provides no means for conveniently locating a bar code label.

SUMMARY OF THE INVENTION

The present invention relates to evaporation closures useful for minimizing evaporation from containers, particularly automated clinical analyzer reagent bottles.

In one embodiment of the present invention the closure (closure A) comprises:

a cap, made of pliable material, comprising a top wall having an opening, a skirt downwardly depending from the top wall and having a threadless internal wall adapted to slip on and sealingly engage a container, and biasing means integral with the skirt; and an elongated arm, comprising a means for sealing the opening, pivotally attached to the cap for movement between a first position wherein the sealing means seals the opening and a second position wherein the sealing means does not seal the opening, the arm being biased toward the first position by the biasing means.

In another embodiment of the present invention the closure (closure B) comprises:

a cap, made of pliable material, comprising:
  a top wall, having an opening;
  a skirt, downwardly depending from the top wall and having a threadless internal wall adapted to slip on and sealingly engage a container;
  an elongated arm, comprising sealing means for sealing the opening, pivotally attached to the top wall for movement between a first position wherein the sealing means seals the opening and a second position wherein the sealing means does not seal the opening; and
  a biasing means, integral with the skirt for biasing the arm toward the first position.

In another embodiment of the present invention the closure (closure C) comprises:
  a top wall, having an opening;
  a skirt, made of pliable material, downwardly depending from the top wall and having a threadless internal wall adapted to slip on and sealingly engage a container;
  an elongated arm, comprising sealing means for sealing the opening, pivotally attached to the top wall for movement between a first position wherein the sealing means seals the opening and a second position wherein the sealing means does not seal the opening; and
  a biasing means, integral with the skirt for biasing the arm toward the first position.

Another embodiment of the present invention relates to any of closures A-C wherein the threadless internal wall has an inverted circumferential ledge having a first diameter proximate the inside of the top wall and a second diameter greater than the first diameter distal the inside of the top wall.

Another embodiment of the present invention relates to any of closures A-C wherein the elongated arm comprises:
  an elongated rigid lever, comprising a second hinge portion, pivotally engaged with a first hinge portion, integral with the top wall, for motion between the first and second positions;
  a washer mounting extension, attached to the elongated rigid lever; and
  a sealing washer attached to the washer mounting extension wherein the sealing washer seals the opening when the lever is in the first position and does not seal the opening when the lever is in the second position.

Another embodiment of the present invention relates to a kit (kit A) for conveniently assembling a closure which comprises in packaged combination:
  a cap, made of pliable material, comprising a top wall having an opening, a skirt downwardly depending from the top wall and having a threadless internal wall adapted to slip on and sealingly engage a container, and biasing means integral with the skirt; and
  an elongated arm, comprising a means for sealing the opening, and adapted to be pivotally attached to the cap for movement between a first position wherein the sealing means seals the opening and a second position wherein the sealing means does not seal the opening, the arm being biased toward the first position by the biasing means.

The present invention, among other advantages, provides for machine operable evaporation closures, eliminates the need for perforable sealing means, and provides for cap position independent machine readable label location. These advantages are realized without requiring machine specific reagent packaging.

BRIEF DESCRIPTION OF THE DRAWINGS

FIG. 1 is a perspective view of a reagent bottle showing a closure of the present invention and a shipping and handling cap.

FIG. 2 is an exploded perspective view of a closure of the present invention.

FIG. 3 is a side view of the closure of FIG. 2.

FIG. 4 is a cross-section view of the closure of FIG. 3 in a closed position along line A—A.

FIG. 5 is a cross-section view of the closure of FIG. 3 in an open position along line A—A.

FIG. 6 is an exploded perspective view of the closure of FIG. 2 with the biasing means retracted.

FIG. 7 is a perspective view of a reagent bottle showing an alternative closure.

FIG. 8 is a cross-section view of the bottle and closure of FIG. 7 along line B—B.

DESCRIPTION OF THE SPECIFIC EMBODIMENTS

Before describing certain specific embodiments of the invention, a number of terms will be defined.

Reagent Bottle — a container, jar, vial, bottle, or the like, having a vertically oriented opening and which is capable of functioning together with a clinical analyzer. Preferably, the opening is an optionally threaded cylindrical neck and the bottle is adapted to stand vertically without support (e.g. it has a flat bottom). The capacity is generally less than about 25 oz., preferably less than about 10 oz., more preferably it will be about 1 oz.

The bottle can be made of any suitable material that does not adversely impact the reagents to be contained in such a manner as to substantially affect the assay to be performed and which is capable of containing the reagents for their expected shelf life. For cost considerations, the material is typically glass or plastic, preferably plastic, more preferably moldable plastic such as high density poly(ethylene) (HDPE). In the event that glass bottles are more cost effective, glass is a more preferred material.

The reagent bottle is generally equipped with a cap or other sealing device to contain the reagents during shipment and handling. Preferably the lid is a screw cap engaged with the threads of the neck, more preferably a screw cap having a retaining ring to prevent inadvertent opening of the bottle.

Rigid material — any moldable material that does not substantially bend during intended use as an elongated arm in the instant device. Typically, such material includes moldable plastics and glass, preferably plastic, more preferably a poly(carbonate). Poly(carbonate)s useful for making elongated arms include Lexan (General Electric), Makrolon (M & B Plastics), Rowlex (Rowland Products), Celanex (Celanese Plastics), Merlon (Mobay Chemical), Sinvet (Anic, Idemitsu technology), Orgalan (ATO Chimie), Panlite (Teijin), Jupilon (Mitsubishi Gas Chemical), Novarex (Mitsubishi Chemical), and Taflon (Idemitsu, not currently producing, production capacity acquired by Mitsubishi Chem.). Lexan (General Electric) is a particularly preferred rigid material.

Pliable material — generally flexible poly(elastomer) having a Shore Hardness of from about 55A to 85A, preferably, from about 60A to 80A, more preferably, from about 65A to 75A. For cost considerations the material is moldable, preferably, injection moldable. The mold shrinkage generally should be less than about 5.0%, preferably, less than about 3%, more preferably less than about 2%. Typically, the mold shrinkage of injection moldable materials having a Shore Hardness of from about 65A to 75A is 1-2%.

A further practical consideration involved in the selection of suitable pliable material for closures wherein the biasing means is comprised of such pliable material is set/creep rate. Set/creep rate, as used herein, is the tendency of a molded pliable material to change shape in response to a force or load. The biasing means of the present invention applies a pre-load to seal force. Pre-load to seal, as use herein, is a force exerted by the biasing means upon the sealing means in a direction that results in the movement of the sealing means into a position that seals the opening in the top wall. Opening the closure, therefore, involves overcoming the pre-load to seal applied by the biasing means. Set/creep can have an affect on the pre-load to seal applied by the biasing means. For example, a molded biasing means used to apply a force upon an elongated arm could, over time, as a result of set/creep, apply a reduced pre-load to seal.

Suitable materials have a set/creep rate less than about 45%, preferable less than about 35%, more preferably less than about 25%, so as to apply a sufficient pre-load to seal after at least a one month period. Generally, the pliable material of the present invention applies a pre-load to seal of from about 25g to 75g, preferably from about 35g to 65g, more preferably from about 45g to 55g. However, the required pre-load to seal is, of course, dependent on the particular application contemplated and the precise design of the closure. Particularly, the biasing means can be adjusted to yield the desired pre-load to seal for any pliable material otherwise suitable as defined herein.

A particular application may require the use of a specific material. Such application may arise, for example, due to a requirement for resistance to chemical degradation. In such an event the material may display otherwise undesirable set/creep characteristics, as, for example, due to an extremely long shelf life requirement. Any adverse impact upon pre-load to seal related to set/creep rate can be minimized or eliminated by providing the closure in kit form. The kit can comprise in packaged combination the necessary components for conveniently assembling the closure prior to use. The kits of the present invention, therefore, are useful, not only for conveniently assembling the instant closures, but also for extending the range of useful pliable materials.

By way of example and not limitation, a number of pliable materials are described below.

1. Santoprene, 271-64 (Monsanto)
   1.1 Hardness: 64A
   1.2 Comp Set: 36%, 168 hr., 100° C.
   1.3 Mold temp: ~200° C.
   1.4 Shrinkage: 1.5-2.0%
2. J-Plast, 1000-64A or 1000-70A SBS (J-Von)
   2.1 Hardness : 64A or 70A respectively
   2.2 Comp set: 17%, 22 hr., 23° C.
   2.3 Mold temp: ~200° C.
   2.4 Shrinkage: 1.0-2.0%
3. Hercuprene 5100-65A or 5100-73A (J-Von)
   3.1 Hardness: 65A or 73A respectively
   3.2 Comp Set: 28% or 31% respectively, 22 hr., 70° C.
   3.3 Mold temp: ~199° C.
   3.4 Shrinkage: 1.0-2.0%
4. Pellethane (polyetherurethane), 2103-70A (Dow)
   4.1 Hardness: 72A
   4.2 Comp Set: 75%, 22 hr., 70° C.
   4.3 Mold temp: ~190° C.
   4.4 Shrinkage: 1.4-1.8%
5. Morthane (polyesterurethane), PS49-300 (Morton)
   5.1 Hardness: 70-75A
   5.2 Comp Set: 70%, 2 hr., 70° C.
   5.3 Mold temp: ~199° C.
   5.4 Shrinkage: N/A
6. Estane (polyesterurethane), 58122 (BFGoodrich)
   6.1 Hardness: 77A
   6.2 Comp Set: 84%, 22 hr., 70° C.
   6.3 Mold temp: ~193° C.
   6.4 Shrinkage: 1.5%
7. Geon (vinyl) (BFGoodrich)
   7.1 Hardness: No. 8812, 63A No. 8813, 75A No 86153, 62A No. 86154, 72A Among the above materials, Santoprene, J-Plast, Morthane, and Estane are preferred. Santoprene is among the most preferred materials for use in an evaporation closure for clinical analyzer reagent bottles. In addition to its desirable mechanical properties, Santoprene has been approved by the FDA for external use in food products although such approval may not be required for use in an evaporation closure.

Optionally, a simple laboratory test can be performed, which can aid in confirming that the set/creep rate properties of a candidate material are acceptable for a particular application and thus further direct the selection of a suitable pliable material. The mechanical properties of interest, generally bending, are measured for a simple model such as a cantilever beam, both initially and at some later time (selected to simulate shelf-life expectations). The change in the property over time is then attributed to the embodiment to be actually used. In this manner an estimation of impact of set/creep rate can be made for the actual embodiment contemplated. For example, when a simple cantilever beam of Santoprene was bent at ambient temperature under a 200g initial load, the material deflection became asymptotic at 0.012-0.013" (20-25%). After 2 weeks the asymptotic deflection occurred at 168-175g. Therefore, considering that in the embodiment of FIGS. 2-6 the load required to deflect the biasing means to its normal open operating position is about 60-80g with an initial deflection of about 0.38", even if the biasing means deflects asymptotic to 0.095" (25%) there is remaining sufficient spring force to seal.

Seal Material — materials that are capable of sealing the opening in the top wall of the closure. Such materials are selected not only based on cost but also based on resistance to an undesirable effects of exposure to the reagents contained in the reagent bottles. Preferably, seal material will be an elastomer. Suitable elastomers include natural rubbers such as latex, acrylic elastomers, butyl rubbers, chlorosulfonated poly(ethylene)s, ethylene-propylene rubbers, fluorinated elastomers, neoprenes, nitrile rubbers, poly(butadiene)s, poly(ether)s, poly(isoprene)s, poly(pentenamer)s, styrene-butadiene rubbers, and thermoplastic elastomers. More preferred elastomers are the inexpensive materials such as natural rubber or latex. Specialty cross-linked materials with advantageous properties may be used when cost permits or when required. Such specialty materials include poly(dimethylsiloxane) having a wide useful temperature range, and resistance to aging, ozone, and light; fluoroelastomers having resistance to heat, oils and chemicals; poly(acrylates) having resistance to oil, oxygen, ozone and light; and ethylene-acrylic polymers having resistance to oils, ozone and chemicals. Preferred seal materials for clinical analyzer applications are natural rubber or latex.

DESCRIPTION OF THE CLOSURES

Referring to FIG. 1, reagent bottle 1 is shown with shipping and handling cap 2 exploded to one side, closure 3 sealingly attached in place of shipping and handling cap 2, and machine readable label 4.

Referring to FIG. 2, closure 3 has a cap 5, made of pliable material and an elongated arm 6. Referring to FIGS. 2-6, cap 5 has a top wall 7 having an opening 8, a skirt 9, downwardly depending from top wall 7, a biasing means 10, and an optional vial locating tap 11. Skirt 9 has a threadless internal wall 12, optionally having an inverted circumferential ledge 13. Skirt 9 is adapted to slip on and sealingly engage a container, typically a bottle with a threaded neck.

When ledge 13 is present, then the threadless internal wall has a first diameter above ledge 13 and near its connection with top wall 7 that is smaller than a second diameter below ledge 13 and away from top wall 7. The location and size of ledge 13 are selected to best engage the reagent bottle to be used. Preferably, ledge 13 is located less than about two thirds of the way down internal wall 12 from top wall 7, more preferably, less than about one half of the way down, still more preferably, less than about one third of the way down. Preferably, the ratio of the diameter of internal wall 12 below ledge 13 to the diameter of internal wall 12 above ledge 13 is less than 1.25 to 1.00, more preferably less than about 1.15 to 1.00, still more preferably less than about 1.10 to 1.00. Optional inverted circumferential ledge 13 is a preferred embodiment of threadless internal wall 12 when the container to be sealed is a bottle having a threaded neck. When ledge 13 is present, the diameter of internal wall 12 is narrower above ledge 13 than below and thus internal wall 12 is better adapted to seal a bottle having a standard threaded neck, which increases in diameter as it extends downward away from the bottle opening. It is, of course, within the purview of the present invention to have more than one circumferential ledge 13 on threadless internal wall 12.

The elongated arm 6 has a sealing means 14, which is capable of sealing opening 8 in top wall 7 of cap 5. The elongated arm 6 should be adapted to attach to cap 5 to allow motion between a first position in which sealing means 14 seals opening 8 and a second position in which sealing means 14 does not seal opening 8. FIG. 4 shows elongated arm 6 in a first, closed or sealed position and FIG. 5 shows elongated arm 6 in a second, open or unsealed position. The freedom to select any means for adapting elongated arm 6 to top wall 7 for such motion is one of the advantages of the present invention.

Preferably, elongated arm 6 is adapted to pivotally attach, connect or engage top wall 7 to allow the required motion between the two positions. In a preferred structure, which allows such pivotal motion, top wall 7 has an integral first hinge portion 15 and elongated arm 6 has a second hinge portion 16 adapted to pivotally engage first hinge portion 15. A preferred first hinge portion 15 has one or more hinge pin receiving holes 17, more preferably two hinge pin receiving holes 17. A preferred second hinge portion 16 has one or more hinge pins 18 adapted to slidably engage one or more hinge pin receiving holes 17, more preferably two hinge pins 18.

The biasing means 10 biases elongated arm 6 toward the first position in which sealing means 14 seals opening 8. Preferably, the biasing means will be integral with cap 5, more preferably, it will be integral with skirt 9. The biasing means 10 will generally be an integral molded strip of pliable material from which cap 5 is constructed. The simplicity and cost effectiveness of molding a single part from pliable material which contains top wall 7, skirt 9 and biasing means 10 is one of the advantages of the present invention. Such a structure provides for the required elasticity of both skirt 9 and biasing means 10.

Vial locating tab 11 is a strip of material disposed, positioned, attached, connected, or the like, between skirt 9 and biasing means 10. Preferably, tab 11 is integral with skirt 9 and biasing means 10. The width of biasing means 10 and skirt 9 are greater than that of tab 11 such that a recess, groove, channel, or the like, is formed between biasing means 10 and skirt 9. A rack, tray, transport, carousel, or the like, which has a vertical wall having a slot, notch, cut out, or the like, having substantially parallel edges extending generally downward from the top edge or surface of the rack can be adapted to slidably engage tab 11. Once engaged, the bottle attached to the closure will be maintained in a defined position within the rack.

Sealing means 14 may be a surface of any shape, e.g. flat, hemispherical, or the like, which is capable of sealing opening 8 when elongated arm is in a first, closed position. It may be molded into elongated arm 6 or it may be a separate piece attached to elongated arm 6. When sealing means 14 is a single piece, it may be a molded surface e.g. a disk or a hemisphere integral with elongated arm 6 and adapted to sealing engage opening 8 when elongated arm 6 is in the first, closed position. When sealing means 14 is a separate part, elongated arm 6 has a means for mounting it. Seal mounting means may be any means adapted to receive a seal. Preferably, the mounting means is an extension attached to elongated arm 6 having a seal retaining support.

Sealing means 14 is preferably a separate part such as a washer, gasket, o-ring, or the like. A washer is a more preferred separate sealing part. In a structure where sealing means 14 is a washer, elongated arm 6 has rigid lever 6, second hinge portion 16 as described above, and washer mounting extension 19 attached to rigid lever 6. Washer mounting extension 19 has a washer mounting pin 20 adapted to receive a washer 21. Washer mounting extension 19 and washer mounting pin 20 taken together constitute the seal mounting means. Second hinge portion 16 is pivotally engaged with top wall 7. Preferably, second hinge portion 16 is engaged with first hinge portion 15 such that the rigid arm may move between a first and second position as described above. More preferably, rigid lever 6 has first and second ends, second hinge portion 16 is formed integrally at the first end, and washer mounting extension 19 is adapted to receive a Washer and is attached to rigid lever 6 between second hinge portion 16 and the second end. Sealing washer 21 is attached to washer mounting extension 19 such that it seals opening 8 when rigid lever 6 is in a first position but does not seal opening 8 when rigid lever 6 is in a second position.

In an alternative embodiment, cap 5 is made of pliable material and includes top wall 7 and skirt 9. The preferred structures for top wall 7 and skirt 9 (e.g. first hinge portion 15 and inverted circumferential ledge 13) described above are also preferred for an embodiment of this type. In such an embodiment, biasing means 10 is made from a material other than the pliable material of the cap and may be attached to skirt 9. Preferably, it will be integral with the skirt. Biasing means of this type may be a spring such as a flexible metallic or plastic torsion spring molded into the cap but not made of the same material as the cap. Such an embodiment can be prepared in a manner similar to that described below for the preferred embodiment. The material of the biasing means is placed into a mold (e.g. an open injection mold), the mold is be prepared to receive the pliable material (e.g. an injection mold would be closed), and the pliable material is added to the mold (e.g. injected into an injection mold). Once removed from the mold, the cap has an integral biasing means made from material other than the pliable material of the cap.

In another alternative embodiment, skirt 9 is made of pliable material and both top wall 7 and biasing means 10 are made of material other than that of skirt 9. The preferred structures for top wall 7 and skirt 9 (e.g. first hinge portion 15 and inverted circumferential ledge 13) described above are also preferred for an embodiment of this type. Such an embodiment can be made in a manner similar to that outlined above for the first alternative embodiment.

The flexibility of independently selecting the materials of construction of skirt 9, top wall 7 and biasing means 10 is one of the advantages of the present invention. Once selected, the materials can be molded into a single cost effective piece.

In another alternative embodiment, sealing means 14 can be adapted to not only seal reagent bottle 1 as described above, but also to perform one or more steps for preparing reagent bottle 1 for use. For example, reagent bottle 1, in addition to shipping and handling cap 2, may be equipped with an auxiliary seal (e.g. a plastic or metal foil seal or membrane secured across the opening of reagent bottle 1). In this event, sealing means 14 can have a means for perforating the auxiliary seal such as washer mounting pin 20 extended to reach and penetrate the auxiliary seal. When a closure of this type is attached to a reagent bottle having an auxiliary seal, it perforates the seal and prepares the reagent bottle for use.

FIGS. 7 and 8 relate to less preferred alternative embodiments of the invention. Closures of this type, in addition to top wall 7 having opening 8, elongated arm 6, having sealing means 14, and vial locating tab 11, all as defined above; have a mechanical biasing means 10 (e.g. a metallic or plastic spring) and a means for threaded engagement of a threaded neck of reagent bottle 1. Preferably, the means for threaded engagement is an inner threaded sleeve 22 adapted to attach to an outer sleeve 23 to allow outer sleeve 23 to rotate freely when threaded inner sleeve 22 is fully engaged with the threaded neck of reagent bottle 1. More preferably, outer sleeve 23 rotates freely (relative to threaded inner sleeve 22) when threaded inner sleeve 22 is fully engaged with the threaded neck of reagent bottle 1 and a downward force (as depicted by the vertical arrow in FIG. 8) is not applied to the closure. In this way, the closure may be threaded onto reagent bottle 1 and, by releasing any downward force and rotating outer sleeve 23, elongated arm 6 may be aligned with machine readable label 4. Further, this more preferred closure of the embodiments of FIGS. 7 and 8 is easily removed from reagent bottle 1 by application of a downward force while rotating outer sleeve 23 in the direction required for unthreading threaded inner sleeve 22.

DESCRIPTION OF THE KITS

The kits of the present invention include in packaged combination component parts necessary to conveniently assemble the closures described. Certain readily available components that may be required to assemble the closures such as washers, o-rings, gaskets, or the like, can be included or excluded from the kits. In this way, the kits may include only the parts of the closures such as the caps and elongated arms that are not otherwise available. The kits may have the closures available in partially assembled form as, for example, a washer may be mounted on a washer mounting extension or an elongated arm may be mounted on a cap. Assembly or partial assembly of the components is performed as described.

A typical kit (kit A) for conveniently assembling a closure may include in packaged combination:
  a cap, made of pliable material, comprising a top wall having an opening, a skirt downwardly depending from the top wall and having a threadless internal wall adapted to slip on and sealingly engage a container, and biasing means integral with the skirt; and
  an elongated arm, comprising a means for sealing the opening, and adapted to be pivotally attached to the cap for movement between a first position wherein the sealing means seals the opening and a second position wherein the sealing means does not seal the opening, the arm being biased toward the first position by the biasing means.

Each of the preferred closure components discussed above is also a preferred component for inclusion in a kit of the present invention.

In another kit embodiment, the threadless internal wall has an inverted circumferential ledge having a first diameter at the top wall and a second diameter greater than the first diameter away from the top wall.

In another kit embodiment, the cap further comprises a vial locating tab disposed between and integral with the biasing means and the skirt and having a width less than the diameter of the skirt and less than the width of the biasing means.

In another kit embodiment, the sealing means comprises a washer mounting extension, attached to the elongated arm and adapted to receive a sealing washer.

In another kit embodiment, kit A further comprises in packaged combination a sealing washer, adapted to be attached to a washer mounting extension, attached to the elongated arm and adapted to receive a sealing washer.

In another kit embodiment, the top wall further comprises an integral first hinge portion, adapted to be pivotally engaged with the elongated arm for motion between the first and second positions.

In another kit embodiment, the elongated arm further comprises an integral second hinge portion, adapted to be pivotally engaged with a first hinge portion, integral with the top wall, for motion between the first and second positions.

In another kit embodiment, the elongated arm comprises:
  an elongated rigid lever, comprising a second hinge portion, adapted to be pivotally engaged with the first hinge portion for motion between the first and second positions; and a washer mounting extension attached to the elongated rigid lever and adapted to receive a sealing washer.

PREPARATION OF CLOSURES

The individual components of the present invention can be prepared in a variety of ways such as machining or stamping components from blocks or sheets of material, extruding and cutting linear strips of material and assembling with glue or solvent/heat welded joints, casting or molding powdered or fluid material, or the like. Preferably, the components other than washers, o-rings, gaskets, or the like, that are otherwise available, are molded, more preferably, they are injection molded. Preferably, the washers, or the like, when not otherwise available, are stamped or cut from commercially available stock.

By way of illustration and not limitation, one molding process for making one piece caps of the present invention that are entirely made from pliable material utilizes a mold composed of:

- a mold bottom that forms skirt 9, threadless internal wall 12 with optional circumferential ledge 13, and the lower surface of top wall 7;
- a mold top that forms the top surface of biasing means 10, the top portion Of first hinge portion 15, and a portion of the top surface of top wall 7;
- a biasing means slide that forms the bottom surface of biasing means 10 and an additional portion of the top surface of top wall 7;
- two hinge pin receiving hole slides that form hinge pin receiving holes 17, the side portion of first hinge portion 15, and the remaining portions of the top surface of top wall 7; and
- an ejector rod that pushes rough molded caps free of the mold bottom.

The process includes the steps of:
closing the injection mold;
filling the closed mold with liquid pliable material;
heating the mold until the pliable material is cured;
cooling the mold containing the cured pliable material;
lifting the mold top to release the top surface of biasing means 10, the top portion of first hinge portion 15, and a portion of top wall 7;
retracting the biasing means slide to release the bottom surface of biasing means 10 and an additional portion of the top surface of top wall 7;
retracting the hinge pin receiving hole slides simultaneously or in sequence to release the sides of first hinge portion 15, hinge pin receiving holes 17, and the remaining portion of the top surface of top wall 7;
extending the ejector to eject the rough molded cap from the mold bottom; and
cleaning any gates or other waste material from the rough molded cap to form the finished molded cap.

The elongated arm is generally made from rigid material. Washers, when present, are generally made from seal material, both as defined above. It is contemplated that those embodiments in which the sealing means is integrally molded into elongated arm 6 do not require a washer or other like part. In such cases the sealing means is a molded surface e.g. a disk or a hemisphere integral with elongated arm 6 and adapted to sealing engage opening 8 when elongated arm 6 is in a first, closed position.

Certain embodiments of the invention may be susceptible to fabrication as a single component. In such a case, no further assembly may be required. However, when assembly is required, the components may be assembled or supplied in kit form as described above.

Referring to FIG. 6, assembly steps generally include pivotally engaging elongated arm 6 with top wall 7 and mounting of sealing means 14 on a sealing means mounting extension if required. Preferably, the pivotal engagement of elongated arm 6 with top wall 7 involves engaging first hinge portion 15 of top wall 7 with second hinge portion 16 of elongated arm 6. By way of example and not limitation, first hinge portion 15 is adapted to receive second hinge portion 16 when biasing means 10 is in a fully retracted position. FIG. 5 shows such a retracted position. Hinge pins 18 of second hinge portion 16 may be slidably engaged with hinge pin receiving holes 17 of first hinge portion 15 from the biasing means side of first hinge portion 15. In such an exemplary embodiment, the biasing means, when restored to an unretracted position, acts to not only bias elongated arm 6 toward the first, closed position, but also to retain the engagement of first hinge portion 15 and second hinge portion 16.

Mounting of washer 21 on a washer mounting extension 19 may involve pressing washer 21 onto a mounting pin 20.

USE OF CLOSURES

The present invention relates particularly to machine operable evaporation closures useful for clinical analyzer reagent bottles. Such reagent bottles are typically supplied in capped form. FIG. 1 shows reagent bottle 1 and typical shipping and handling cap 2 supplied to seal reagent bottle 1 during shipment and handling. Shipping and handling cap 2 is removed from reagent bottle 1 prior to use in an analyzer. Once removed, shipping and handling cap 2 is replaced by closure 3 in accordance with the present invention. Replacement involves attaching closure 3 to reagent bottle 1 in such a manner as to seal reagent bottle 1. Preferably, closure 3 slips on and downwardly depending skirt 9, having threadless internal wall 12, sealingly engages reagent bottle 1. The preferred closure is, therefore, capable of sealing a reagent bottle without being threaded into place. The ability to sealingly engage a reagent bottle with a threadless internal skirt wall is one of the advantages of the present invention.

Once secured to reagent bottle 1, the closure may be manipulated, as by rotation, to align an optional machine readable label 4 (e.g. a bar code label) in such a manner as to allow the analyzer to both read label 4 and operate closure 3. The ability of the operator to conveniently align a bar code or other label by simply rotating or twisting the closure such that the machine can both read the label and operate the closure is one of the advantages of the present invention.

Machine operation of closure 3 involves application of a closure opening force to elongated arm 6 as depicted by way of example and not limitation in FIG. 5 by the horizontal arrow representing a force applied to elongated arm 6. The force can be applied by any closure opening means capable of being machine controlled. The opening means is typically a mechanical means such as a push rod or roller bar. It is contemplated that reagent bottle 1 and closure 3 can be stationary and the operating means movable or that the opening means be stationary and reagent bottle 1 be movable as by, for example, rotation of a bottle rack or carousel as commonly employed in clinical analyzers. The sealing of reagent bottle 1 is accomplished by the removal of the force. Removal typically involves retraction of an opening means or rotation of a bottle rack or carousel beyond or past a fixed opening means. The capacity of the present closures to be opened by a variety of means including stationary and movable means is one of the advantages of the present invention.

When the contents or shelf life of a reagent bottle are exhausted, the low cost and simplicity of the present closures allows for the bottle and closure to be properly disposed of either together or separately or individually recycled. Alternatively, the closures can be cleaned for re-use. If an opened reagent bottle 1, sealed by closure 3, is not immediately required for a particular analysis, it can be either conveniently stored without removing the closure or it can be sealed by a separate cap such as the shipping and handling cap. The choice presented to the operator to either store the bottle with the machine operable closure of the invention or with another sealing means is one of the advantages of the present invention.

What is claimed is:

1. A closure comprising:
    a cap made of pliable material comprising (a) a top wall having an opening, (b) a skirt, downwardly depending from said top wall, said skirt made of pliable material and having a threadless internal wall to slip on and sealingly engage a container, and (c) a discrete first hinge portion integral with said top wall;
    an elongated arm comprising sealing means for sealing said opening and a discrete second hinge portion integral with said elongated arm, said discrete second hinge portion pivotally mated with said discrete first hinge portion and rotatable relative thereto for movement of said elongated arm between a first position, wherein said sealing means seal said opening and a second position, wherein said sealing means does not seal said opening
    biasing means having a width and integral with said skirt for biasing said arm toward said first position; and
    a vial locating tab separate from said hinge portions and disposed between and integral with said biasing means and said skirt, said vial locating tab having a width less than an outside diameter of said skirt and less than the width of said biasing means.

2. The closure of claim 1 wherein said threadless internal wall has an inverted circumferential ledge having a first diameter at said top wall and a second diameter greater than said first diameter away from said top wall.

3. The closure of claim 1 wherein said sealing means comprises a washer.

4. The closure of claim 1 wherein said elongated arm comprises:
    a washer mounting extension, attached to said elongated arm, and
    a sealing washer attached to said washer mounting extension wherein said sealing washer seals said opening when said lever is in said first position and does not seal said opening when said lever is in second position.

5. The closure of claim 1 wherein said pliable material is a poly(elastomer).

6. A kit for conveniently assembling a closure which kit comprises in packaged combination:
    (a) a cap made of pliable material, comprising a top wall having an opening, a skirt having an outside diameter and downwardly depending form said top wall and having an threadless internal wall to slip on and sealingly engage a container, said top wall having a discrete first hinge portion, and biasing means having a
    (b) an elongated arm comprising sealing means for sealing said opening and a discrete second hinge portion integral with said elongated arm, said discrete second hinge portion pivotally mated with said discrete first hinge portion and rotatable relative thereto for movement of said elongated arm between a first position, wherein said sealing means seals said opening and a second position, wherein said sealing means does not seal said opening, said elongated arm being biased toward said first position by said biasing means;
    a vial locating tab separate from said hinge portions and disposed between and integral with said biasing means and said skirt, said vial locating tab having a width less than an outside diameter of said skirt and less than the width of said biasing means.

7. The kit of claim 6 wherein said threadless internal wall has an inverted circumferential ledge having a fist diameter at said top wall and a second diameter greater than said first diameter away from said top wall.

8. The kit of claim 6 wherein said sealing means comprises a washer mounting extension, attached to said elongated arm and adapted to receive a sealing washer.

9. The kit of claim 8 which further comprises in packaged combination a sealing washer, adapted to be attached to said washer mounting extension.

10. The kit of claim 6 wherein said elongated arm comprises:
    a washer mounting extension attached to said elongated arm and adapted to receive a sealing washer.

11. The kit of claim 10 which further comprises in packaged combination a sealing washer adapted to be attached to said washer mounting extension wherein said sealing washer seals said opening when said lever is in said first position and does not seal said opening when said lever is in said second position.

12. The closure of claim 6 wherein said pliable material is a poly(elastomer).

* * * * *